United States Patent
Yoshimatsu et al.

(10) Patent No.: US 11,998,031 B2
(45) Date of Patent: Jun. 4, 2024

(54) STABILIZATION OF ENZYME TREATED ROYAL JELLY

(71) Applicant: Yamada Bee Company, Inc., Okayama (JP)

(72) Inventors: Maiko Yoshimatsu, Okayama (JP); Yurino Takada, Okayama (JP); Aya Komai, Okayama (JP)

(73) Assignee: Yamada Bee Company, Okayama (JP)

( * ) Notice: Subject to any disclaimer, the term of this patent is extended or adjusted under 35 U.S.C. 154(b) by 840 days.

(21) Appl. No.: 17/042,670

(22) PCT Filed: Mar. 22, 2019

(86) PCT No.: PCT/JP2019/012057
§ 371 (c)(1),
(2) Date: Sep. 28, 2020

(87) PCT Pub. No.: WO2019/188774
PCT Pub. Date: Oct. 3, 2019

(65) Prior Publication Data
US 2021/0120853 A1   Apr. 29, 2021

(30) Foreign Application Priority Data

Mar. 28, 2018  (JP) ................. 2018-063169

(51) Int. Cl.
| | | |
|---|---|---|
| *A23L 21/20* | (2016.01) | |
| *A23L 29/238* | (2016.01) | |
| *A23L 29/244* | (2016.01) | |
| *A23L 29/256* | (2016.01) | |
| *A23L 29/269* | (2016.01) | |
| *A61K 35/644* | (2015.01) | |
| *A61K 47/36* | (2006.01) | |

(52) U.S. Cl.
CPC ............. *A23L 21/20* (2016.08); *A23L 29/238* (2016.08); *A23L 29/244* (2016.08); *A23L 29/256* (2016.08); *A23L 29/269* (2016.08); *A61K 35/644* (2013.01); *A61K 47/36* (2013.01)

(58) Field of Classification Search
None
See application file for complete search history.

(56) References Cited

FOREIGN PATENT DOCUMENTS

| | | | |
|---|---|---|---|
| CN | 102579501 | A | 7/2012 |
| JP | 2002/112715 | A | 4/2002 |
| JP | 2005/287411 | A | 10/2005 |
| JP | 2006/280249 | A | 10/2006 |
| JP | 2007/295919 | A | 11/2007 |
| JP | 2007/295920 | A | 11/2007 |
| JP | 2008/194031 | A | 8/2008 |
| JP | 4182366 | B | 11/2008 |
| JP | 2011/152103 | A | 8/2011 |
| JP | 2015/091767 | A | 5/2015 |
| JP | 2016/214192 | A | 12/2016 |
| WO | WO-2018/034268 | A1 | 2/2018 |

OTHER PUBLICATIONS

English translation of Kawatake (CN 101223946 A (2008) ).*

* cited by examiner

*Primary Examiner* — Susan Hoffman
(74) *Attorney, Agent, or Firm* — Cesari & McKenna, LLP

(57) ABSTRACT

Disclosed are an enzyme-treated royal jelly composition comprising carrageenan and enzyme-treated royal jelly treated with a peptidase; an enzyme-treated royal jelly composition comprising at least one member selected from the group consisting of galactomannan, galactomannan-containing polysaccharides, and xanthan gum, at least one member selected from the group consisting of carrageenan, dextrin, and pullulan, and enzyme-treated royal jelly treated with a peptidase; and an enzyme-treated royal jelly composition comprising dextrin, at least one member selected from the group consisting of carrageenan and pullulan, and enzyme-treated royal jelly treated with a peptidase.

4 Claims, 1 Drawing Sheet

| Evaluation | Color name | CMYK | RGB | HEX | Color | No. |
|---|---|---|---|---|---|---|
| -- | Milky white | C0, M5, Y20, K0 | rgb(255,242,204) | #fff2cc | | 1 |
| | | C0, M5, Y30, K0 | rgb(255,242,179) | #fff2b3 | | 2 |
| | | C0, M10, Y35, K0 | rgb(255,229,166) | #ffe5a6 | | 2.5 |
| ± | Milky yellow | C0, M15, Y40, K0 | rgb(255,215,154) | #ffd79a | | 3 |
| | | C0, M10, Y40, K5 | rgb(242,218,145) | #f2da91 | | 3.5 |
| | | C0, M15, Y45, K10 | rgb(230,195,126) | #e6c37e | | 4 |
| | | C0, M17, Y48, K15 | rgb(217,180,113) | #d9b471 | | 4.5 |
| + | Orange brown | C0, M20, Y50, K20 | rgb(204,163,102) | #cca366 | | 5 |
| | | C0, M25, Y55, K30 | rgb(179,134,80) | #b38650 | | 6 |
| | | C0, M30, Y60, K40 | rgb(153,107,61) | #996b3d | | 7 |
| ++ | Dark brown | C0, M40, Y80, K40 | rgb(153,92,31) | #995c1f | | 8 |
| | | C0, M50, Y80, K50 | rgb(128,64,25) | #804019 | | 9 |
| | | C0, M60, Y100, K60 | rgb(102,41,0) | #662900 | | 10 |
| | | C0, M84, Y100, K70 | rgb(76,12,0) | #4c0c00 | | 11 |
| +++ | Blackish brown | C0, M100, Y100, K75 | rgb(64,0,0) | #400000 | | 12 |
| | | C0, M100, Y100, K80 | rgb(50,0,0) | #320000 | | 13 |
| ++++ | Black | C0, M100, Y100, K91 | rgb(24,0,0) | #180000 | | 14 |
| | | C0, M100, Y100, K95 | rgb(12,0,0) | #0c0000 | | 15 |

STABILIZATION OF ENZYME TREATED ROYAL JELLY

CROSS-REFERENCE TO RELATED APPLICATIONS

This application is the National Stage of International Application No. PCT/JP2019/012057, filed on Mar. 22, 2019, which claims priority to Japanese Application No. 2018-063,169, filed on Mar. 28, 2018, the contents of both prior applications being hereby incorporated by reference in their entirety.

TECHNICAL FIELD

The present invention relates to an enzyme-treated royal jelly composition with suppressed moisture absorption. Further, the present invention relates to a method for suppressing moisture absorption of enzyme-treated royal jelly that occurs over time.

BACKGROUND ART

Royal jelly is a useful natural ingredient; on the other hand, however, it is known to cause allergic reactions in some cases. Therefore, various methods have been studied to decompose or lower the molecular weight of protein, which can be an allergen, to reduce the amount of allergen.

For example, as methods for reducing the amount of allergen in royal jelly, in other words, as methods for preparing low-allergenized royal jelly, the following have been proposed: a method of subjecting royal jelly to a glycolytic enzyme treatment and a protease treatment (PTL 1), a method of subjecting royal jelly to an endo-type neutral peptidase treatment (PTL 2), a method of subjecting royal jelly to a one-step enzyme treatment with an alkaline peptidase having both endopeptidase action and exopeptidase action (PTL 3), a method of treating royal jelly with an enzyme having endopeptidase action and an enzyme having exopeptidase action simultaneously or sequentially (PTL 4), and the like.

However, low-allergenized royal jelly whose protein is decomposed by a peptidase (enzyme-treated royal jelly) is more susceptible to temperature and humidity than royal jelly that is not treated with enzymes, and coloring proceeds under severe conditions, such as heating and humidification, resulting in browning. Such coloring is considered to be due to the Maillard reaction that occurs between the amide groups of peptides and amino acids fragmented by enzyme-treatment and the anomeric carbon of the reducing sugar.

As a method for suppressing coloring of enzyme-treated royal jelly, PTL 5 has reported a method in which enzyme-treated royal jelly is allowed to coexist with locust bean gum. Further, PTL 6 has reported that discoloration of the appearance over time can be prevented by dissolving royal jelly and at least one member selected from starch and dextrin having a dextrose equivalent of 18 or less in a solvent, followed by freeze-drying.

CITATION LIST

Patent Literature

PTL 1: JP2002-112715A
PTL 2: JP2005-287411A
PTL 3: JP2007-295919A
PTL 4: JP2007-295920A
PTL 5: JP4182366B
PTL 6: JP2011-152103A

SUMMARY OF INVENTION

Technical Problem

However, enzyme-treated royal jelly problematically has higher moisture absorption than royal jelly that is not enzyme-treated. High moisture absorption causes particle cracking etc., and leads to reduction of operability etc.

An object of the present invention is to provide an enzyme-treated royal jelly composition that contains enzyme-treated royal jelly treated with a peptidase but has suppressed moisture absorption, and particularly a freeze-dried enzyme-treated royal jelly composition. Another object of the present invention is to provide a method for suppressing moisture absorption of enzyme-treated royal jelly.

Solution to Problem

As a result of intensive studies to achieve the above objects, the present inventors found that when enzyme-treated royal jelly is allowed to coexist with at least one member selected from the group consisting of carrageenan, dextrin, pullulan, gum arabic, and xanthan gum, the moisture absorption thereof over time can be significantly prevented. Further, they found that coloring can also be prevented, in addition to the prevention of moisture absorption.

The present invention has been completed upon further studies based on these findings. The present invention provides the following enzyme-treated royal jelly composition, method for producing the enzyme-treated royal jelly composition, and method for suppressing moisture absorption of enzyme-treated royal jelly.

(I) Enzyme-Treated Royal Jelly Composition (I-1) A solid enzyme-treated royal jelly composition comprising carrageenan and enzyme-treated royal jelly treated with a peptidase.

(I-2) An enzyme-treated royal jelly composition comprising carrageenan in an amount of more than 1 mass %, and enzyme-treated royal jelly treated with a peptidase.

(I-3) An enzyme-treated royal jelly composition comprising enzyme-treated royal jelly treated with a peptidase, and carrageenan in an amount of more than 1 part by mass per 100 parts by mass of the enzyme-treated royal jelly.

(I-4) An enzyme-treated royal jelly composition comprising:

at least one member selected from the group consisting of galactomannan, galactomannan-containing polysaccharides, and xanthan gum;

at least one member selected from the group consisting of carrageenan, dextrin, and pullulan; and enzyme-treated royal jelly treated with a peptidase.

(I-5) An enzyme-treated royal jelly composition comprising:

dextrin;

at least one member selected from the group consisting of carrageenan and pullulan; and enzyme-treated royal jelly treated with a peptidase.

(I-6) The enzyme-treated royal jelly composition according to (I-4), wherein the galactomannan-containing polysaccharide is at least one member selected from the group consisting of locust bean gum, tara gum, and fenugreek gum.

(I-7) The enzyme-treated royal jelly composition according to any one of (I-1) to (I-6), wherein the composition is a lyophilizate.

(II) Method for Producing Enzyme-Treated Royal Jelly Composition (II-1) A method for producing the enzyme-treated royal jelly composition according to any one of (I-1) to (I-3), comprising adding carrageenan before, at the same time as, or after peptidase treatment of royal jelly.

(II-2) A method for producing the enzyme-treated royal jelly composition according to (I-4), comprising adding at least one member selected from the group consisting of galactomannan, galactomannan-containing polysaccharides, and xanthan gum, and at least one member selected from the group consisting of carrageenan, dextrin, and pullulan, before, at the same time as, or after peptidase treatment of royal jelly.

(II-3) A method for producing the enzyme-treated royal jelly composition according to (I-5), comprising adding dextrin and at least one member selected from the group consisting of carrageenan and pullulan, before, at the same time as, or after peptidase treatment of royal jelly.

(II-4) The production method according to (II-2), wherein the galactomannan-containing polysaccharide is at least one member selected from the group consisting of locust bean gum, tara gum, and fenugreek gum.

(II-5) A method for producing the enzyme-treated royal jelly composition according to (I-7), wherein freeze-drying is further performed in the production method according to any one of (II-1) to (II-4).

(III) Method for Suppressing Moisture Absorption of Enzyme-Treated Royal Jelly (III-1) A method for suppressing moisture absorption of enzyme-treated royal jelly, comprising adding at least one member selected from the group consisting of carrageenan, dextrin, pullulan, gum arabic, and xanthan gum, before, at the same time as, or after peptidase treatment of royal jelly so that the enzyme-treated royal jelly is allowed to coexist with the at least one member selected from the group consisting of carrageenan, dextrin, pullulan, gum arabic, and xanthan gum.

(III-2) A method for suppressing moisture absorption and coloring of enzyme-treated royal jelly, comprising adding at least one member selected from the group consisting of carrageenan, dextrin, pullulan, gum arabic, and xanthan gum, before, at the same time as, or after peptidase treatment of royal jelly so that the enzyme-treated royal jelly is allowed to coexist with the at least one member selected from the group consisting of carrageenan, dextrin, pullulan, gum arabic, and xanthan gum.

(III-3) A method for suppressing moisture absorption of enzyme-treated royal jelly, comprising:
adding at least one member selected from the group consisting of carrageenan, dextrin, pullulan, gum arabic, and xanthan gum, before, at the same time as, or after peptidase treatment of royal jelly; and
freeze-drying the enzyme-treated royal jelly in the coexistence of the at least one member selected from the group consisting of carrageenan, dextrin, pullulan, gum arabic, and xanthan gum.

(III-4) A method for suppressing moisture absorption and coloring of enzyme-treated royal jelly, comprising:
adding at least one member selected from the group consisting of carrageenan, dextrin, pullulan, gum arabic, and xanthan gum, before, at the same time as, or after peptidase treatment of royal jelly; and
freeze-drying the enzyme-treated royal jelly in the coexistence of the at least one member selected from the group consisting of carrageenan, dextrin, pullulan, gum arabic, and xanthan gum.

Advantageous Effects of Invention

The present invention can provide an enzyme-treated royal jelly composition in which moisture absorption caused by peptidase decomposition is suppressed while improving safety by reducing allergenicity. Further, the present invention can provide an enzyme-treated royal jelly composition in which coloring is suppressed at the same time as suppression of moisture absorption.

BRIEF DESCRIPTION OF DRAWING

FIG. 1 is a view showing a color chart used in Test Example 2.

DESCRIPTION OF EMBODIMENTS

The present invention is explained in detail below.

In this specification, the terms "contain" and "comprise" encompass the meanings of "essentially consist of" and "consist of."

(1) Enzyme-Treated Royal Jelly Composition and Method for Producing the Same

The enzyme-treated royal jelly composition of the present invention has the following features (a) to (e):

(a) comprising carrageenan and enzyme-treated royal jelly treated with a peptidase, and being solid;

(b) comprising carrageenan in an amount of more than 1 mass % (or in an amount of 1.5, 2, 3, 3.5, 5, or 10 mass % or more) and enzyme-treated royal jelly treated with a peptidase;

(c) comprising enzyme-treated royal jelly treated with a peptidase, and carrageenan in an amount of more than 1 part by mass (or in an amount of 1.5, 2, 3, 3.5, 5, 10, or 200 parts by mass or more) per 100 parts by mass of the enzyme-treated royal jelly;

(d) comprising at least one member selected from the group consisting of galactomannan, galactomannan-containing polysaccharides, and xanthan gum; at least one member selected from the group consisting of carrageenan, dextrin, and pullulan; and enzyme-treated royal jelly treated with a peptidase; and (e) comprising dextrin; at least one member selected from the group consisting of carrageenan and pullulan; and enzyme-treated royal jelly treated with a peptidase.

In the enzyme-treated royal jelly composition, moisture absorption is suppressed in the enzyme-treated royal jelly. In addition, the production of brown substances is suppressed to prevent the progress of browning. In that sense, the enzyme-treated royal jelly composition is stabilized over time.

In the feature (d) above, galactomannan and galactomannan-containing polysaccharides do not have a high moisture absorption-suppressing effect, as shown in the Examples provided later; however, they do not interfere with the moisture absorption-suppressing effects of carrageenan, dextrin, and pullulan. Therefore, an excellent effect of suppressing moisture absorption and coloring can be obtained as the enzyme-treated royal jelly composition.

Royal jelly is a milky jelly-like material formed by mixing secretions secreted from the hypopharyngeal and mandibular glands of 3- to 12-day-old worker bees among honey bees. Examples of the main bioactive components in royal jelly include organic acids, such as 10-hydroxy decenoic acid (hereinbelow referred to as "decenoic acid") that is specific to royal jelly; proteins; lipids; saccharides; vitamins, such as vitamin B, folic acid, nicotinic acid, and pantothenic acid; various minerals; and the like. Known bioactive and pharmacological effects of royal jelly include antimicrobial effects, immune-enhancing effects, antidepressant effects, antitumor effects, anti-inflammatory effects, blood flow increase effects, and the like. Additionally, reduction in side effects of anticancer drugs, and effects of extending life in radiation damage have also been reported.

The royal jelly used in the production of enzyme-treated royal jelly is not particularly limited. Examples include raw royal jelly, royal jelly powder obtained by drying and powderizing raw royal jelly, an extract obtained by extracting raw royal jelly using water or water-containing ethanol, and the like.

The production areas of royal jelly are not limited, and examples include Japan, China, Brazil, European countries, Oceania countries, the United States, and the like.

The enzyme-treated royal jelly of the present invention is a product formed by treating royal jelly with a protease. Preferred is enzyme-treated royal jelly having reduced allergenicity in which allergic reaction due to the protein in the royal jelly is suppressed by a peptidase treatment. Accordingly, the enzyme-treated royal jelly of the present invention includes, in addition to a peptidase-decomposed product of protein contained in the royal jelly, decenoic acid and like organic acids, lipids, saccharides, vitamins, and various minerals as mentioned above.

A preferable enzyme used for enzyme-treating royal jelly may be a peptidase. The peptidase to be used only needs to have at least one of endopeptidase action and exopeptidase action. A peptidase having at least endopeptidase action is preferred, and a peptidase having both actions is more preferred.

The enzyme-treated royal jelly of the present invention is preferably obtained by subjecting protein contained in royal jelly to hydrolyzation to thereby reduce allergenicity. To obtain such enzyme-treated royal jelly, it is preferable to hydrolyze royal jelly by using a peptidase (endopeptidase) having at least endopeptidase action, and preferably by using a peptidase having both endopeptidase action and exopeptidase action. As a peptidase having both endopeptidase action and exopeptidase action, a peptidase simultaneously having both actions can be used singly, or a peptidase (endopeptidase) having endopeptidase action and a peptidase (exopeptidase) having exopeptidase action can be used in combination.

In the present invention, any endopeptidase can be used as long as it is a protease having at least endopeptidase activity. For example, various endopeptidases derived from animals (e.g., trypsin and chymotrypsin), endopeptidases derived from plants (e.g., papain), and endopeptidases derived from microorganisms (e.g., lactobacilli, yeast, fungi, *Bacillus subtilis*, and actinomycetes) can be used.

Any exopeptidase can be used as long as it is a protease having at least exopeptidase activity. Examples include carboxypeptidase, aminopeptidase, and exopeptidases derived from microorganisms (e.g., lactobacilli, fungi of the genus *Aspergillus*, and fungi of the genus *Rhizopus*). Pancreatin and pepsin, each of which also has endopeptidase activity, can also be used.

Peptidases include exopeptidases substantially having exopeptidase action alone, endopeptidases substantially having endopeptidase action alone, and peptidases having both exopeptidase action and endopeptidase action. Of these, enzymes having both exopeptidase action and endopeptidase action can be used as endopeptidases when the endopeptidase action is strong, can be used as exopeptidases when the exopeptidase action is strong, and can be used as peptidases simultaneously having exopeptidase action and endopeptidase action when the endopeptidase action is equal to, or substantially equal to, the exopeptidase action.

Of such peptidases, preferred examples of the enzyme having exopeptidase action include a peptidase produced with *Aspergillus oryzae*, a peptidase produced with *Aspergillus sojae*, a peptidase produced with the genus *Aspergillus*, and a peptidase produced with *Rhizopus oryzae*.

Preferred examples of the peptidase having endopeptidase action include a peptidase produced with *Bacillus subtilis*, a peptidase produced with *Bacillus licheniformis*, a peptidase produced with *Bacillus stearothermophilus*, a peptidase produced with *Bacillus amyloliquefaciens*, and a peptidase produced with the genus *Bacillus*.

Further, preferred examples of the peptidase having both exopeptidase action and endopeptidase action, particularly preferred examples of alkaline peptidases, include a peptidase produced with *Streptomyces griseus*, a peptidase produced with *Aspergillus oryzae*, and a peptidase produced with *Aspergillus melleus*. Since an enzyme treatment using such a peptidase allows protein to be broken into a lower molecular compound by one-step enzyme treatment, the operation is simple, and it is advantageously possible to prevent loss and significant reduction in the bioactivity of effective components contained in the royal jelly.

The amount of peptidase relative to royal jelly varies depending on the concentration of the royal jelly to be used, enzymatic titer, reaction temperature, and reaction time, and cannot be generalized. In general, it is preferable to use the peptidase in a proportion of 50 to 10000 unit per gram of protein in royal jelly. In this case, the peptidase may be added to the royal jelly at once, or gradually and separately.

The pH of the royal jelly in the peptidase treatment can be selected from a pH range of 2 to 12, preferably a pH range of 7.5 to 10, and more preferably a pH range of 7.8 to 9, according to the optimal pH range of the enzyme to be used. Specifically, before the peptidase is added to the royal jelly, depending on the kind of the enzyme to be used, the pH of the royal jelly is adjusted to a desired range, i.e., a pH of 2 to 12, preferably a pH of 7.5 to 10, and more preferably a pH of 7.8 to 9, by adding an acid, alkali agent, or buffer. In this case, examples of acids include hydrochloric acid, sulfuric acid, nitric acid, phosphoric acid, acetic acid, and the like; examples of alkaline agents include sodium hydroxide, potassium hydroxide, potassium carbonate, and the like; and examples of buffers include phosphoric acid buffers, citric acid buffers, and the like.

The temperature of the peptidase treatment is not particularly limited. The temperature may be generally selected from the range of practical use including an optical temperature range at which peptidase action, preferably endopeptidase action, and more preferably both endopeptidase action and exopeptidase action are exhibited, i.e., the range between 30 and 70° C. By maintaining the temperature at a temperature lower or higher than the optimum peptidase temperature (preferably about 40 to 55° C.), e.g., the range between 50 and 60° C., decay in the step of peptidase treatment can be avoided. The time for the peptidase treatment depends on the kind of the enzyme to be used and reaction conditions, such as reaction temperature and pH, and is not particularly limited.

The royal jelly can be subjected to a protease treatment without any treatment or after being dissolved or dispersed in water. If the royal jelly is in a dried form, it is preferably subjected to a protease treatment after being dissolved in water.

The peptidase treatment is stopped by deactivating or removing the peptidase. Deactivation operation can be conducted by using a heating treatment (e.g., at 80° C. for 15 minutes).

As described above, the enzyme-treated royal jelly of the present invention may be royal jelly that is treated with at least a peptidase. The enzyme-treated royal jelly of the present invention also includes royal jelly that is treated with a combination of a peptidase and other enzyme(s), e.g., a peptidase and a glycolytic enzyme.

The carrageenan used in the present invention is a polysaccharide obtained from red algae, and is composed of galactose, anhydrogalactose, sulfuric acid, and the like.

The pullulan used in the present invention is a water-soluble polysaccharide produced by *Aureobasidium pullulans*, and having a structure in which maltotrioses having α-1,4-linked three glucose molecules are α-1,6-linked.

The dextrin used in the present invention is a polysaccharide obtained by hydrolyzing starch with acid, enzyme, heat, or the like. Examples of dextrin include malt dextrin, dextrin, cyclodextrin, indigestible dextrin, and the like. Further, the dextrin equivalent (DE) is not particularly limited, and dextrin having any DE can be used.

The xanthan gum used in the present invention is a polysaccharide produced by *Xanthomonas campestris*, and is composed of glucose, mannose, and glucuronic acid.

The gum arabic (arabic gum) used in the present invention is a polysaccharide secreted from the bark of *Acacia senegal* and the like, and is composed of galactose, arabinose, rhamnose, and glucuronic acid.

The galactomannan used in the present invention refers to a wide range of polysaccharides composed of D-galactose and D-mannose. Specifically, galactomannan has a structure in which galactose residues are α-1,6-linked as side chains to the main chain (mannan) of β-1,4-linked mannose residues. The proportion of mannose residues and galactose residues is not particularly limited.

Further, in the present invention, polysaccharides containing galactomannan may also be used instead of or in combination with galactomannan. Examples of such polysaccharides preferably include polysaccharides containing galactomannan as a main component, and specifically locust bean gum, guar gum, tara gum, fenugreek gum, and the like. Locust bean gum, tara gum, and fenugreek gum are preferable, and locust bean gum is more preferable. These polysaccharides can be used singly or in any combination of two or more.

The galactomannan-containing polysaccharides targeted by the present invention include polysaccharides containing other sugars such as D-glucose, in addition to galactomannan and its constituent sugars D-galactose and D-mannose. Such polysaccharides may contain galactomannan in a proportion of about 50% or more, and contain D-galactose, D-mannose, and other sugars as the remaining components.

The proportion of the above polysaccharides (which refer to "carrageenan, dextrin, pullulan, gum arabic, xanthan gum, galactomannan, and galactomannan-containing polysaccharides"; hereinafter the same) contained in the enzyme-treated royal jelly composition of the present invention is, as the total amount thereof, 0.1 to 200 parts by mass, 1 to 100 parts by mass, 1 to 10 parts by mass, or 200 parts by mass or more, per 100 parts by mass (solid content) of the enzyme-treated royal jelly contained in the enzyme-treated royal jelly composition. If the amount of these components is too small, suppression of moisture absorption and coloring is reduced.

The proportion of the polysaccharides contained in the enzyme-treated royal jelly composition of the present invention is, as the total amount thereof, an amount of more than 1 mass %, 1.5 mass % or more, 2 mass % or more, 3 mass % or more, or 10 to 90 mass %.

The enzyme-treated royal jelly composition of the present invention can be produced by adding the above polysaccharides before, after, or at the same time as peptidase treatment of royal jelly. The enzyme-treated royal jelly composition of the present invention is preferably produced by adding and mixing the polysaccharides after peptidase treatment of royal jelly, that is, with the enzyme-treated royal jelly.

The enzyme-treated royal jelly composition of the present invention is not particularly limited in its form, and may be liquid or solid, but preferably has a freeze-dried form. The lyophilizate can be prepared by adding and mixing the polysaccharides before, after, or at the same time as peptidase treatment of royal jelly, preferably with the enzyme-treated royal jelly after peptidase treatment, and then freeze-drying the resultant. The freeze-drying process can be carried out according to a standard method.

The enzyme-treated royal jelly composition of the present invention thus prepared may be in the form of liquid agents, such as drinks and syrups, or lyophilizates (e.g., freeze-dried powder); or suitable additives may be added thereto to form tablets, chewable tablets, capsules, granules, and the like.

(2) Method for Suppressing Moisture Absorption of Enzyme-Treated Royal Jelly

The method for suppressing moisture absorption of enzyme-treated royal jelly (or the method for suppressing moisture absorption and coloring) according to the present invention can be carried out by adding at least one member selected from the group consisting of carrageenan, dextrin, pullulan, gum arabic, and xanthan gum, before, at the same time as, or after peptidase treatment of royal jelly so that the enzyme-treated royal jelly is allowed to coexist with the at least one member selected from the group consisting of carrageenan, dextrin, pullulan, gum arabic, and xanthan gum.

The target royal jelly, the type of peptidase used, and the peptidase treatment, as well as the carrageenan, dextrin, pullulan, gum arabic, and xanthan gum used are as described in (1) above.

Further, the method for suppressing moisture absorption of enzyme-treated royal jelly (or the method for suppressing moisture absorption and coloring) can also be carried out by adding at least one member selected from the group consisting of carrageenan, dextrin, pullulan, gum arabic, and xanthan gum to enzyme-treated royal jelly treated with a peptidase; and freeze-drying the enzyme-treated royal jelly in the coexistence of the at least one member selected from the group consisting of carrageenan, dextrin, pullulan, gum arabic, and xanthan gum.

A lyophilizate obtained by this method is an enzyme-treated royal jelly composition suitable in the present invention containing the enzyme-treated royal jelly in a state of suppressing moisture absorption (or suppressing moisture absorption and coloring). The freeze-drying process can also be carried out by the method described in (1).

EXAMPLES

The following describes the present invention in more detail with reference to Examples. However, the present invention is not limited to the Examples.

Examples 1 to 5 and Comparative Examples 1 and 2

500 g of Chinese raw royal jelly was weighed in a 2000 mL beaker, 250 mL of ion-exchanged water was added, and the mixture was stirred until it became homogeneous to prepare a royal jelly diluted solution. A 2 N NaOH aqueous solution was added thereto to adjust the pH of the royal jelly diluted solution to 8.6 to 8.9. Next, a solution prepared by dissolving 5 g of peptidase having both exopeptidase action and endopeptidase action in 50 mL of ion-exchanged water was added to the royal jelly diluted solution, and ion-exchanged water was further added so that the total amount of ion-exchanged water was 500 mL. The reaction mixture was hydrolyzed by reaction at 50 to 55° C. (thermostatic water bath) for 2 hours while stirring with a propeller. Then, the temperature of the thermostatic water bath was raised to 80° C., and the enzyme was inactivated by heating for 15 minutes, after which an enzyme-treated royal jelly (solution) was obtained. 137 g of the enzyme-treated royal jelly solution was weighed in a 300 mL beaker. Then, 0.9 g of each of the polysaccharides shown in Tables 1 to 4 and 1.7 g of crystalline cellulose were added to the beaker according to the following formulation, and the mixture was stirred until it became homogeneous. The resultant was freeze-dried to obtain an enzyme-treated royal jelly composition (lyophilizate) (polysaccharide content of lyophilizate: 3.1 mass %, mass of polysaccharide per 100 parts by mass (solid content) of enzyme-treated royal jelly: 3.4 parts by mass).

Formulation
Enzyme-treated royal jelly solution: 137 g
Polysaccharide: 0.9 g
Crystalline cellulose: 1.7 g

Test Example 1: Moisture Absorption Suppression

The polysaccharide-containing enzyme-treated royal jelly compositions of the Examples and Comparative Examples were each left under airtight conditions (35° C., humidity of 75% RH) and under exposure conditions for 72 hours. The stability (moisture absorption suppression) was evaluated by measuring the changes in weight. The "35° C., humidity of 75% RH" conditions were adjusted using a thermo-hygrostat.

The results of the first test are shown in Table 1, and the results of the second test are shown in Table 2. As shown in Tables 1 and 2, the results revealed that when dextrin, gum arabic, xanthan gum, pullulan, and carrageenan were mixed to form enzyme-treated royal jelly compositions containing polysaccharides, moisture absorption of the enzyme-treated royal jelly was suppressed more than when locust bean gum was mixed.

TABLE 1

| | Type of polysaccharide | Moisture absorption at each elapsed time (changed mass/initial mass) | | | Moisture absorption (72 h) (when Comparative Example 1 is 100) | Comparison with locust bean gum (Comparative Example 1) (72 h) |
|---|---|---|---|---|---|---|
| | | 24 h | 48 h | 72 h | | |
| Example 1 | Dextrin | 8.7% | 10.1% | 10.6% | 66.0% | −34.0% |
| Example 2 | Gum arabic | 8.9% | 10.7% | 11.1% | 69.6% | −30.4% |
| Example 3 | Xanthan gum | 13.6% | 14.9 | 15.1% | 94.6% | −5.4% |
| Example 4 | Pullulan | 12.1% | 13.2% | 13.6% | 84.8% | −15.2% |
| Comparative Example 1 | Locust bean gum | 13.1% | 15.6% | 16.0% | 100.0% | — |

TABLE 2

| | Type of polysaccharide | Moisture absorption at each elapsed time (changed mass/initial mass) | | | Moisture absorption (72 h) (when Comparative Example 2 is 100) | Comparison with locust bean gum (Comparative Example 2) (72 h) |
|---|---|---|---|---|---|---|
| | | 24 h | 48 h | 72 h | | |
| Example 5 | Carrageenan | 10.9% | 11.7% | 11.8% | 91.0% | −9.0% |
| Comparative Example 2 | Locust bean gum | 12.1% | 12.8% | 13.0% | 100.0% | — |

Test Example 2: Coloring Suppression

The polysaccharide-containing enzyme-treated royal jelly compositions of the Examples and Comparative Examples were each left under airtight conditions (35° C., humidity of 75% RH) and under exposure conditions for 72 hours. The degree of coloring was visually observed over time, and the stability (coloring suppression) was evaluated using the color chart shown in FIG. 1. The "35° C., humidity of 75% RH" conditions were adjusted using a thermo-hygrostat.

The results of the first test are shown in Table 3, and the results of the second test are shown in Table 4. As shown in Tables 3 and 4, the results revealed that when dextrin, gum arabic, xanthan gum, pullulan, and carrageenan were mixed to form enzyme-treated royal jelly compositions containing polysaccharides, coloring of the enzyme-treated royal jelly was suppressed as much as when locust bean gum was mixed.

TABLE 3

| | Type of polysaccharide | Color change at each elapsed time | | | | |
|---|---|---|---|---|---|---|
| | | 0 h | 0.5 h | 1 h | 24 h | 48 h |
| Example 1 | Dextrin | 1 | 4 | 4 | 8 | 9 |
| Example 2 | Gum arabic | 1 | 4 | 4 | 8 | 9 |
| Example 3 | Xanthan gum | 1 | 2 | 2 | 6 | 8 |
| Example 4 | Pullulan | 1 | 3 | 3 | 8 | 9 |
| Comparative Example 1 | Locust bean gum | 1 | 3 | 3 | 6 | 8 |

TABLE 4

| | Type of polysaccharide | Color change at each elapsed time | | | | |
|---|---|---|---|---|---|---|
| | | 0 h | 0.5 h | 1 h | 24 h | 48 h |
| Example 5 | Carrageenan | 1 | 2.5 | 2.5 | 6 | 8 |
| Comparative Example 2 | Locust bean gum | 1 | 2 | 2 | 5 | 6 |

The invention claimed is:

1. A method for suppressing moisture absorption of enzyme-treated royal jelly, comprising adding at least one member selected from the group consisting of carrageenan and pullulan to a royal jelly before, at the same time as, or after peptidase treatment of the royal jelly.

2. A method for suppressing moisture absorption and coloring of enzyme-treated royal jelly, comprising adding at least one member selected from the group consisting of carrageenan and pullulan to a royal jelly before, at the same time as, or after peptidase treatment of the royal jelly.

3. A method for suppressing moisture absorption of enzyme-treated royal jelly, comprising:
adding at least one member selected from the group consisting of carrageenan and pullulan to a royal jelly before, at the same time as, or after peptidase treatment of the royal jelly to form an enzyme-treated royal jelly mixture; and
freeze-drying the enzyme-treated royal jelly mixture.

4. A method for suppressing moisture absorption and coloring of enzyme-treated royal jelly, comprising:
adding at least one member selected from the group consisting of carrageenan and pullulan to a royal jelly before, at the same time as, or after peptidase treatment of the royal jelly to form an enzyme-treated royal jelly mixture; and
freeze-drying the enzyme-treated royal jelly mixture.

* * * * *